United States Patent [19]
Altendorf

[11] Patent Number: 5,167,660
[45] Date of Patent: Dec. 1, 1992

[54] HF SURGERY DEVICE

[75] Inventor: Hans-Walter Altendorf, Worms, Fed. Rep. of Germany

[73] Assignee: Siemens Aktiengesellschaft, Munich, Fed. Rep. of Germany

[21] Appl. No.: 668,113

[22] Filed: Mar. 12, 1991

[30] Foreign Application Priority Data

Mar. 27, 1990 [DE] Fed. Rep. of Germany ....... 4009819

[51] Int. Cl.$^5$ .............................................. A61B 17/39
[52] U.S. Cl. ...................................................... 606/40
[58] Field of Search ...................................... 606/37–40

[56] References Cited

U.S. PATENT DOCUMENTS

| | | | |
|---|---|---|---|
| 3,812,858 | 5/1974 | Oringer . | |
| 4,574,801 | 3/1986 | Manes | 606/38 |
| 4,590,934 | 5/1986 | Malis et al. | 606/37 |
| 4,658,819 | 4/1987 | Harris et al. | 606/39 X |
| 4,658,820 | 4/1987 | Klicek | 606/40 X |
| 4,739,759 | 4/1988 | Rexroth | 606/39 X |
| 4,961,047 | 10/1990 | Carder . | |
| 4,961,739 | 10/1990 | Thompson | 606/40 X |
| 4,969,885 | 11/1990 | Farin . | |

FOREIGN PATENT DOCUMENTS

| | | |
|---|---|---|
| 0219568 | 4/1987 | European Pat. Off. . |
| 0316469 | 5/1989 | European Pat. Off. . |
| 0336742 | 10/1989 | European Pat. Off. . |
| 3342722 | 5/1984 | Fed. Rep. of Germany . |
| 3830193 | 3/1990 | Fed. Rep. of Germany . |
| 2517955 | 6/1983 | France .................................. 606/39 |
| 2154881 | 1/1985 | United Kingdom . |
| 2164473 | 3/1986 | United Kingdom . |

*Primary Examiner*—Lee S. Cohen
*Attorney, Agent, or Firm*—Hill, Van Santen, Steadman & Simpson

[57] ABSTRACT

A HF surgery device had a microprocessor and a comparator which in combination generate a control signal which acts on a rectified operating voltage, which drive a HF generator. The HF generator can be modulated with a modulation signal. In order to automatically maintain the effective output power at a constant level in the event of a modulation of the HF generator, the microprocessor forms a reference value from the modulation signal and from a prescribed setting signal for setting a HF output power. The reference value is compared to the operating voltage in the comparator for forming the control signal.

9 Claims, 2 Drawing Sheets

HF SURGERY DEVICE

BACKGROUND OF THE INVENTION

1. Field of the Invention

The present invention is directed to a HF surgery device, and in particular to a HF surgery device which includes a microprocessor-controlled circuit to maintain the HF output signal at a constant output power.

2. Description of the Prior Art

HF surgery devices are known in the art which include a microprocessor and a comparator for acting in combination to generate a control signal, the control signal acting on a rectified operating voltage to control the HF output signal. Such a surgery device is disclosed in European application 0 316 469. The HF output signal in this known device can be modulated with a modulation signal. Also in this known surgery device, various reference values for the HF voltage can be supplied to the comparison circuit. The reference values can be pre-programmed, and contained within the microprocessor, and can be selected by an actuating switch, for example, at an electrode handle. The required comparison signal is formed from the HF output voltage, for which purpose an insulating component, for example a transformer, and at least one voltage converter are required. The HF output signal must have a constant level, which is is the case in the event of an amplitude modulation. In this known HF surgery device, a check must be undertaken to determine whether the comparison signal is to be proportional to the peak value, to the effective value, or to an average value of the modulated HF output voltage. Therefore, additional voltage converters are required, which must be activated by the operator as needed.

In order to achieve a deep coagulation, the ratio of the peak voltage to the effective voltage is increased by the modulation, but the effective output power must remain substantially constant. Power increases or decreases arise in the HF output voltage due to the amplitude modulation, the increase or decrease arising in accord with the envelope of the modulation signal. The HF output voltage therefore does not have a constant level in this known apparatus. Consequently, a significant decrease in the available, effective output power occurs due to the valleys in the shape of the output voltage signal which occur, for example, in the event of regulation dependent on the peak value of the HF output voltage. A satisfactory coagulation is thus not possible.

The operator of this known HF surgery device must therefore compensate power drops caused by the modulation by switching to a different voltage converter and to a higher output voltage. There may, however, be difficulties related to such switching insofar as a non-linear relationship exists between the operating voltage an the HF output power. A less skillful operator of the HF surgery device can be easily overburdened with this selection and setting of the suitable parameters.

SUMMARY OF THE INVENTION

It is an object of the present invention to provide an HF surgery device with which the effective output power can be automatically maintained constant over a wide range with low outlay for components when switching to a modulated HF output signal.

It is a further object of the present invention to provide such a surgery device wherein auxiliary equipment, for example equipment for monitoring the output signal, is simultaneously automatically matched to the modulated HF output signal.

The above objects are achieved in accordance with the principles of the present invention in an HF surgery device having a microprocessor and a comparator which in combination generate a control signal which acts on a rectified operating voltage which supplies an HF generator. The HF generator can be modulated with a modulation signal. The microprocessor forms a reference value from the modulation signal and from a prescribed setting signal for setting the HF output power. The reference value is compared to the operating voltage in the comparator, which forms the control signal based on the comparison. The HF output power is thereby maintained at a constant level, even in the event of a modulation.

Neither an insulating transformer nor voltage converters for generating a comparison signal are required in the HF surgery device disclosed herein. Because the reference value formed in the microprocessor (microcomputer) according to the invention is calculated from a setting signal for the preselected HF output power dependent on a modulation signal, all manual matching activity in view of the effective HF output power is eliminated for the operator when switching to a modulated HF output signal. This important advantage of the invention is also present in the event of a modification of the modulation signal, for example, for varying the coagulation depth. The shape of the modulation signal is known or can be calculated in the microprocessor. The microprocessor can therefore generate a reference value which takes all parameters into consideration which change due to the modulation.

In a further embodiment of the invention, further setting, correction and/or auxiliary signals which, particularly in the event of a modulated HF output signal, act on auxiliary equipment such as, for example, monitoring, display and/or instrument illumination means for enhancing the precision, can be formed from the modulation signal using the microprocessor. The modulation signal is also capable of being generated in the microprocessor, which eliminates the need for a separate generator for the modulation signal.

DESCRIPTION OF THE PREFERRED EMBODIMENTS

Figure 1:
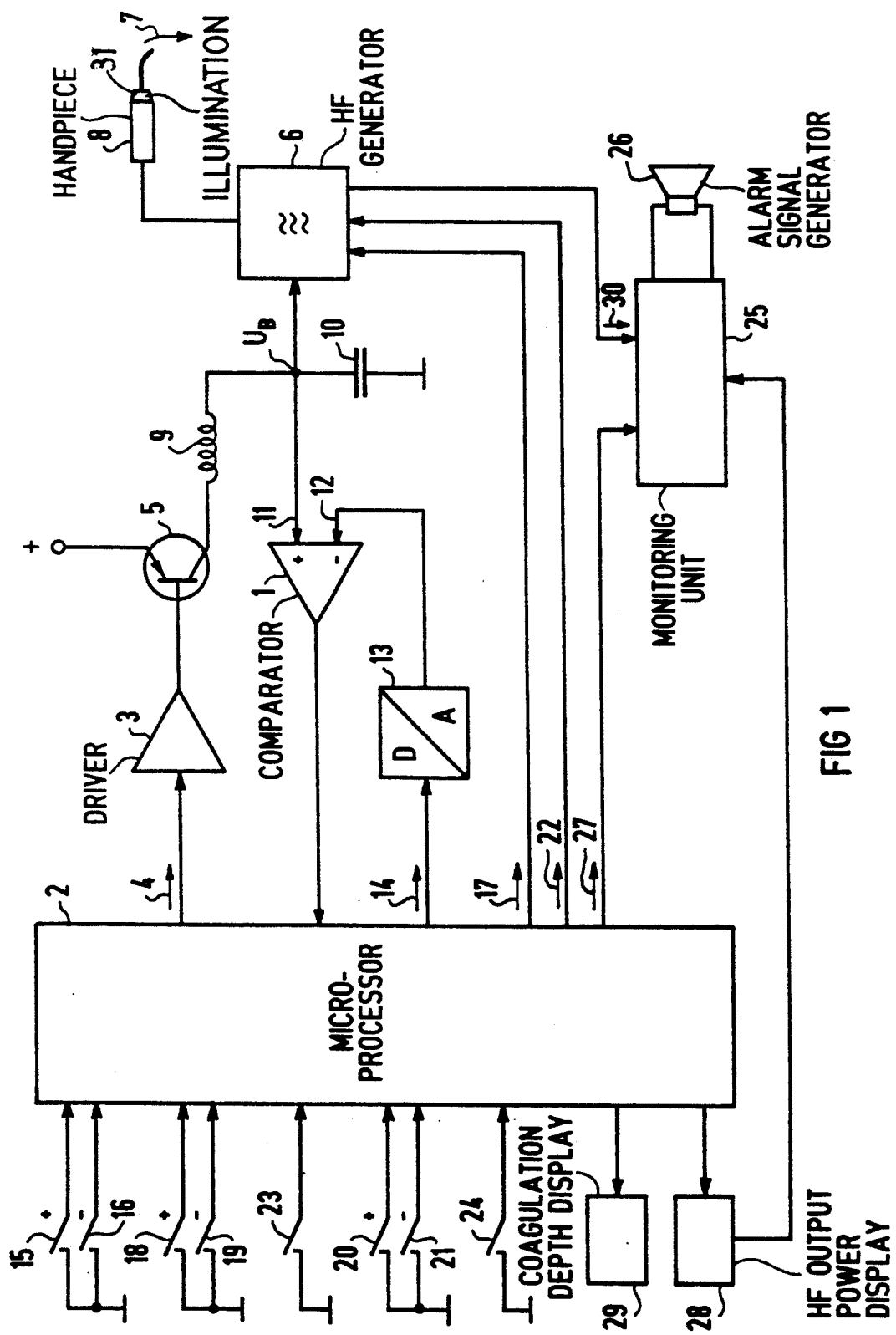
FIG. 1 is a schematic block diagram of a HF surgery device constructed in accordance with the principles of the present invention.

In the HF surgery device shown in FIG. 1, a comparator 1 has an output connected to a microprocessor 2, forming in combination a comparison circuit which generates a control signal 4. The control signal 4 is a binary signal having a pulse frequency greater than or equal 20 kHz and having a pulse duration which can be set by the microprocessor 2.

The control signal 4 controls and stabilizes a rectified operating voltage $U_B$ of a HF generator 6, via control means formed by a driver 3 and a power transistor 5. The HF generator 6, which may be a multi-stage unit, generates a HF output signal 7 which, via a handpiece 8 having a surgical electrode, is available for acting on biological tissue. The transistor 5 is not linearly operated, but is instead operated in a switched mode, so that a filter circuit formed by a coil 9 and a capacitor 10 is provided in order to generate a constant operating voltage $U_B$ for the HF generator 6, for example for the output stage thereof.

The operating voltage $U_B$ is also supplied to an input 11 of the comparator 1. The comparator 1 has another input 12 to which a reference value 14, digitally generated in the microprocessor 2, is supplied as an analog signal via a digital-to-analog converter 13. The reference value 14 is generated in the microprocessor 2 from a setting signal which is prescribed via switches 15 and 16 for setting the HF output power, and from a binary modulation signal 17 having a frequency of, for example, 200 Hz. The binary modulation signal 17 modulates the HF generator 6, for example by activating and deactivating an operating voltage, such as the controlled operating voltage $U_B$.

An increase or a reduction of the preselectable, effective HF output power is established by a duration-dependent actuation of the switches 15 or 16 via the microprocessor 2.

Figure 2:
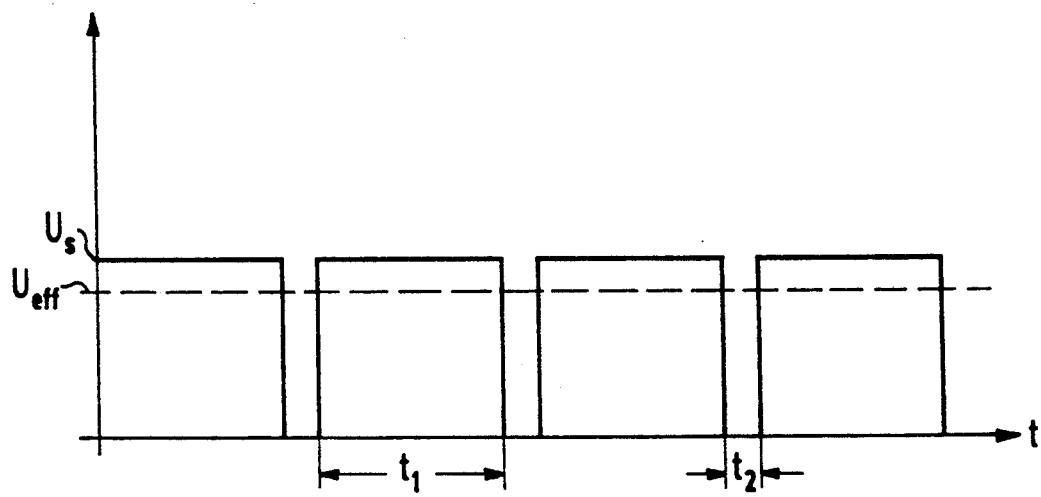
FIGS. 2 and 3 respectively show envelopes of differently modulated HF output signals as may occur in the HF surgery device shown in FIG. 1.
Figure 3:
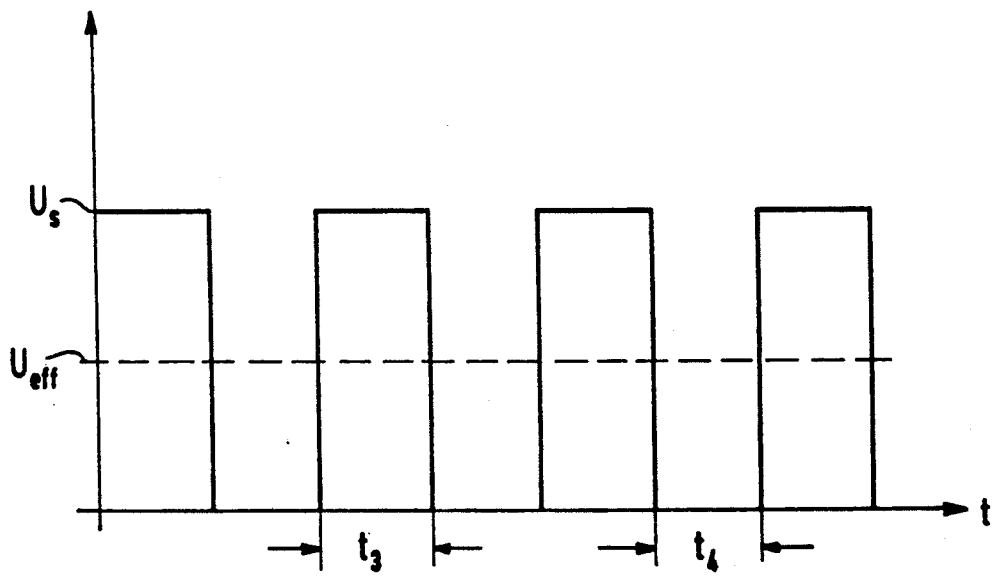

Switches 18 and 19, with which the coagulation depth can be continuously adjusted via the microprocessor 2, are preferably disposed at the handpiece 8. To that end, a setting of the pulse width $t_1$ or $t_3$ of the individual pulses in undertaken by a duration-dependent actuation of the switches 18 or 19. For example, a modulation signal can be generated in the microprocessor 2 which is composed of a square-wave pulse sequence having a defined clock frequency, as shown in FIGS. 2 and 3.

Components for switching the modulation signal 17 can be eliminated by making the pulse width $t_1$ (FIG. 2) or $t_3$ (FIG. 3) of such a size that pulse pauses $t_2$ to $t_4$ are eliminated, so that a continuous signal is present, as a result of which the HF generator 6 generates a constant (unmodulated) HF output signal. The HF generator 6, consequently, may also be switched on with the modulation signal. The modulation signal may also be supplied to the microprocessor 2 from a separate generator (not shown) for example as a rectified, unfiltered a.c. voltage.

Further signals decoupled from one another for controlling functions in the HF surgery device can be formed in the microprocessor 2 from the modulation signal. For example, a further signal 22, which is independent in pulse width of the modulation signal 17, can serve to control the intensity of an instrument illumination 31 by time-dependent actuation of the switches 20 or 21.

The HF generator 6, and thus the high frequency output signal, can be switched on and off with a switch 23 via the microprocessor 2. After activation of a switch 24, the microprocessor 2 may also control the instrument illumination 31, so that the instrument illumination 31, for example in the handpiece 8, continues to be illuminated for a short time, for example a light seven seconds, after the HF generator 6 is switched off.

A monitoring unit 25 having an alarm signal generator 26 connected thereto, can be controlled by a complementary signal 27 formed from the modulation signal 17 in the microprocessor 2, so that the monitoring unit 25 does not respond during the pulse pauses $t_2$ or $t_4$ in the modulation signal 17, so that false alarms are avoided the complementary signal 27 may also be used for correcting a HF power display 28 in the case of a modulated HF output signal. A coagulation depth display 29 may also be provided without special circuitry for controlling component parts, the display 29 being controlled by the signal 27 as well as the modulation signal 17 from the microprocessor 2. An analog signal 30, derived from the operating voltage $U_B$, may be supplied to the monitoring unit 25, in which case the binary signal 27 can also serve the purpose of forming an effective value.

The envelope of a modulated HF output signal is shown in FIG. 2. The pulse width (pulse duration) $t_1$ of each pulse of the modulation signal 17 is noticeably larger than the short pause having the duration $t_2$ between successive pulses. A relatively slight difference between the peak voltage $U_S$ and the effective voltage $U_{eff}$ of the envelope signal thereby results. Only a slight coagulation depth is therefore achieved.

As shown in FIG. 3, the pulse duration $t_3$ and the pause duration $t_4$ are selected to be the same size, as a result of which a favorable coagulation effect can be achieved. It is clear that, given the same effective voltage $U_{eff}$, the ratio of the respective peak voltages $U_S$ in FIGS. 3 and 2 is different, and is considerably larger in FIG. 3. A deeper coagulation is thus achieved with the HF output signal having the envelope as shown in FIG. 3, without the effective value of the output power, which was already selected, having to be readjusted due to the modulation.

The pulse repetition rate of the modulation signal 17 is selected to be the same in both FIGS. 1 and 2, as can be seen since the leading pulse edges chronologically coincide. As needed, the pulse repetition rate of the modulation signal 17 produced in the microprocessor 2 can also be varied via the microprocessor 2.

The HF surgery device disclosed herein can be used with particular advantage in dental surgery because, among other things, in dental surgery there is a necessity of having to adapt the coagulation depth to the biological tissue quickly and without problems in order to avoid bleeding in the mouth area during surgery.

Although modifications and changes may be suggested by those skilled in the art, it is the intention of the inventor to embody within the patent warranted hereon all changes and modifications as reasonably and properly come within the scope of his contribution to the art.

I claim as my invention:

1. A HF surgery device for use with a source of rectified operating voltage and with a modulation signal generator, comprising:

a microprocessor and a comparator in combination operating as a comparison circuit which generates a control signal as an output;

a HF generator supplied by a rectified operating voltage from said source and being modulable by a modulation signal from said generator;

means for controlling said rectified operating voltage based on said control signal; and said microprocessor including means for forming a reference value from said modulation signal and from a prescribed setting signal which sets an HF output power, said reference value being supplied to said comparator and being compared therein to said operating voltage for forming said control signal to maintain said operating voltage at a substantially constant level.

2. A HF surgery device as claimed in claim 1 wherein said microprocessor includes means for generating said modulation signal as a pulse sequence having pulses therein which modulate said HF generator by successive activation and de-activation of said HF generator.

3. A HF surgery device as claimed in claim 2 wherein said means for generating said modulation signal is a means for generating said modulation signal as a pulse sequence having individual pulses variable in pulse width for changing a coagulation depth achieved by said HF output power.

4. A HF surgery device as claimed in claim 3 further comprising a handpiece connected to an output of said HF generator for administering said HF output power to biological tissue, said handpiece including a plurality of switch means for respectively controlling different functions in said HF surgery device, at least one of said switch means being a means for varying the pulse width of the modulation signal via said microprocessor to eliminate pauses between the pulses to achieve a continuous signal.

5. A HF surgery device as claimed in claim 2 wherein said means for generating said modulation signal is a means for generating a modulation signal as a pulse sequence and wherein said microprocessor further includes means for forming a signal from said modulation signal which is decoupled from said modulation signal and which consists of a plurality of individual pulses having a pulse width which is variable independently of the pulse width of the pulses in the modulation signal.

6. A HF surgery device as claimed in claim 5 further comprising means for monitoring operation of said HF surgery device for generating an alarm signal in the event of malfunction, and wherein said microprocessor includes means for forming a complementary signal from said modulation signal for controlling said means for monitoring.

7. A HF surgery device as claimed in claim 5 wherein said microprocessor includes means for forming a further signal decoupled from said modulation signal consisting of a plurality of individual pulses having a pulse width which is variable independently of the pulse width of the modulation signal.

8. A HF surgery device as claimed in claim 7 further comprising means for illuminating a surgery location to which said HF power is administered, said means for illuminating being controlled by said further signal decoupled from said modulation signal.

9. An HF surgery device as claimed in claim 1 wherein said reference value is a digital signal, and further comprising a digital-to-analog converter connected between said microprocessor and said comparator for converting said digital reference value into an analog signal for supply to said comparator.

* * * * *